(12) United States Patent
Tanaka

(10) Patent No.: US 7,058,985 B2
(45) Date of Patent: Jun. 13, 2006

(54) EAR COVERING AND MANUFACTURING METHOD

(75) Inventor: Masao Tanaka, Setagaya-ku (JP)

(73) Assignee: Metex Corporation, Tokyo (JP)

( * ) Notice: Subject to any disclaimer, the term of this patent is extended or adjusted under 35 U.S.C. 154(b) by 0 days.

(21) Appl. No.: 11/122,437

(22) Filed: May 5, 2005

(65) Prior Publication Data

US 2005/0246816 A1    Nov. 10, 2005

(30) Foreign Application Priority Data

May 7, 2004    (JP)    ............................. 2004-138527

(51) Int. Cl.
*A42B 1/00*    (2006.01)
(52) U.S. Cl. .................. 2/209; 2/174; 2/423; 2/208; 2/411; 2/412; 2/413; 2/414
(58) Field of Classification Search .............. 2/423, 2/209, 208
See application file for complete search history.

(56) References Cited

U.S. PATENT DOCUMENTS

| | | | |
|---|---|---|---|
| 4,872,219 A * | 10/1989 | Duncan | ........................ 2/209 |
| 5,243,709 A * | 9/1993 | Sheehan et al. | ................ 2/209 |
| 5,339,467 A | 8/1994 | Brinkley | |
| 6,055,672 A | 5/2000 | Natvig | |
| 6,298,493 B1 * | 10/2001 | Ambroise | ....................... 2/209 |

* cited by examiner

*Primary Examiner*—John J. Calvert
*Assistant Examiner*—Alissa J. Tompkins
(74) *Attorney, Agent, or Firm*—Howson and Howson

(57) ABSTRACT

An ear covering is produced by sewing first and second cloth layers together along a first closed loop seam, and forming a hole inside the loop and extending through both layers; turning the sewn first and second layers inside out by passing one layer through the opening; then passing one of the layers through a passage in a flexible insert in the form of a distorted, truncated cone; placing a third cloth layer over one of the first and second layers and sewing the first second and third cloth layers along a second closed-loop seam, thereby enclosing the insert within a toroidal enclosure formed by portions of the first and second layers. Afterwards, the assembly is turned inside out to form a cup-shaped receptacle for receiving an external ear, with the second seam in the interior of the receptacle, and with the first seam within the toroidal enclosure.

4 Claims, 4 Drawing Sheets

EAR COVERING AND MANUFACTURING METHOD

FIELD OF THE INVENTION

This invention relates to an ear covering or ear muff, and to a method for manufacturing the same.

BACKGROUND OF THE INVENTION

Conventional ear coverings, aimed primarily at the protection of a wearer's ears in cold weather, comprise a plastic insert having an oval opening for introducing an ear, and a cloth covering stitched along the periphery of the plastic insert as well as at the rim of the oval opening. Precision sewing is required in order to stitch the conventional ear covering, and consequently, a high degree of sewing skill is needed. In addition, in the conventional ear covering, the seams along the periphery of the insert are visible on the outside unless additional measures are taken, such as covering the seam with a bias tape and stitching the bias tape.

U.S. Pat. No. 6,055,672, dated May 2, 2000, discloses an ear covering comprising outer and inner layers, and a cup-shaped plastic insert. This ear covering is produced by first stitching together outer and inner cloth layers placed facing one another. The insert is subsequently provided on the inner cloth layer. Then, a straight slit is cut out in the inner cloth layer, and the cut edges of the slit are turned through the opening of the insert and adhered to the other side of the rim of the insert opening. The manufacturing process is completed by turning the outer cloth layer and the inner layer together with the insert adhered thereon through the insert opening. With this manufacturing method, there is no need to stitch the cloth along the periphery of the insert and the rim of the opening of the insert, and consequently the sewing process is accelerated. In addition, since the stitching along the periphery is hidden inside the ear covering, hemming along the periphery is not required. However, since the cut edges of the inner cloth layer, which are turned through the opening of the insert, are adhered to the insert along the rim of the insert opening, the insert is mostly bare inside of the covering except at the covered rim. Therefore, the wearer's ear may come into direct contact with the bare plastic insert, causing an unpleasant sensation. Moreover, the insulating effect of the ear covering is impaired when the wearer's ear is in direct contact with the bare plastic insert. In addition, after the ear covering is used over a long time, the inner cloth layer may become detached from the insert, and the adhesive agent may come into contact with the wearer's ear. Moreover, although the sewing process is speeded up, the process requires the additional step of adhering the cut edges of the inner cloth layer to the rim of the insert opening. Consequently the manufacturing process is not significantly simplified when compared with the process used in the manufacture of conventional ear coverings.

An object of this invention is to provide an ear covering and manufacturing method where the seams are hidden inside the ear covering, where direct contact between the user's ear and the plastic insert is avoided, where excellent heat insulation and protection are provided, and where the manufacturing process is significantly simplified.

SUMMARY OF THE INVENTION

The ear covering according to the invention comprises first, second and third cloth layers, and an insert with an opening for receiving an external ear. The first and second cloth layers are stitched together along a first seam configured in a closed loop and have first margins extending beyond the first seam. The first, second and third cloth layers are stitched together along a second seam, which is also configured in a closed loop. The second seam is spaced from said first seam, and the first, second and third cloth layers have second margins extending beyond the second seam. Portions of the first and second cloth layers between the first and second seams form a toroidal enclosure, and the insert is situated and enclosed within the toroidal enclosure. The third layer extends across the toroidal enclosure and, with the first and second cloth layers, forms a cup-shaped receptacle for receiving an external ear. The first margins are located within the toroidal enclosure, and the second margins are located inside the cup-shaped receptacle.

Preferably, the insert is composed of a flexible material capable of being shifted, by the application of an external force, from one to the other of two different stable configurations, in each of which the insert is in the shape of a distorted, truncated cone, open at its wide and narrow ends, and having a through passage.

The ear covering is preferably manufactured by the following steps. First the first and second cloth layers are placed in facing relationship to each other, and stitched together along a first seam in the form of a closed loop. An opening is formed through the first and second layers within the closed loop, preferably by forming openings in each layer before the layers are stitched together. The first and second cloth layers are then turned inside out by passing one of the layers through the opening through the first and second layers.

Following the turning step, one of the first and second cloth layers is passed through the passage of the insert so that the insert surrounds the first seam. A third cloth third cloth layer is then positioned adjacent one of the first and second cloth layers and across the opening through the first and second layers.

The first, second and third cloth layers are then stitched together along a second seam in the form of a closed loop surrounding the insert, thereby enclosing the insert within a toroidal enclosure formed by portions of the first and second cloth layers. As a result, an assembly is formed, consisting of the first, second and third cloth layers and the insert. The assembly is turned inside out by passing the third cloth layer at least part way through the insert, thereby forming a cup-shaped receptacle for receiving an external ear. The margins of the first and second layers extending beyond the first seam are located within the toroidal enclosure, and the margins of the first, second and third layers extending beyond the second seam are located within the interior of the cup-shaped receptacle.

The ear covering according to the invention has two important distinguishing features. The seams of the cloth layers are hidden respectively inside the toroidal insert enclosure and within the ear receptacle of the ear covering. The insert is also fully enclosed in the toroidal enclosure formed by the first and second cloth layers. Therefore, the ear covering has a simple appearance, is more comfortable to wear than the conventional ear covering or the ear covering of U.S. Pat. No. 6,055,672, has superior heat insulation, and provides better protection.

The ear covering can be produced by relatively simple sewing operations, and does not require a step of adhering a cloth layer to the rim of an insert using an adhesive agent.

DETAILED DESCRIPTION OF THE PREFERRED EMBODIMENTS

The cloth layers used in the ear covering of the invention can be composed of any of various suitable materials, so long as it has a heat-insulating property. Woven and nonwoven materials can be used, as can knitted materials, felt and fleece-like materials.

Figure 1:
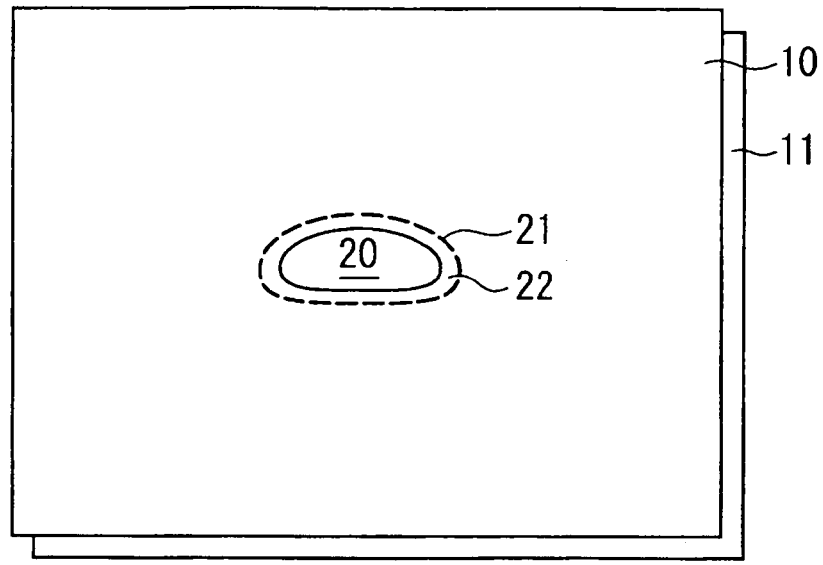
FIG. 1 is a top plan view, showing the stitching of two cloth layers around an insertion hole formed in both of the cloth layers.

A first cloth layer 10 and a second cloth layer 11 are placed face to face, one on top of the other, as shown in FIG. 1. An ear insertion hole 20 is formed in both cloth layers, the hole being composed of two similarly shaped holes the respective cloth layers, the similarly shaped holes being in register with each other. The cloth layer 10 and the cloth layer 11 are stitched together along a seam 21 surrounding the hole 20 and spaced from the hole by a margin 22. The hole 20 can be formed either before or after stitching. However, formation of the hole before stitching is preferred as defines the location at which the stitches are to be formed.

Following the formation of the holes and stitching, the cloth layers are turned inside out by passing one or the other of the cloth layers through hole 20. When the cloth layers are turned inside-out, the stitches are in turned-out parts of the cloth layers which surround the hole, and which located between the main portions of the cloth layers as seen in FIG. 2.

Figure 4:
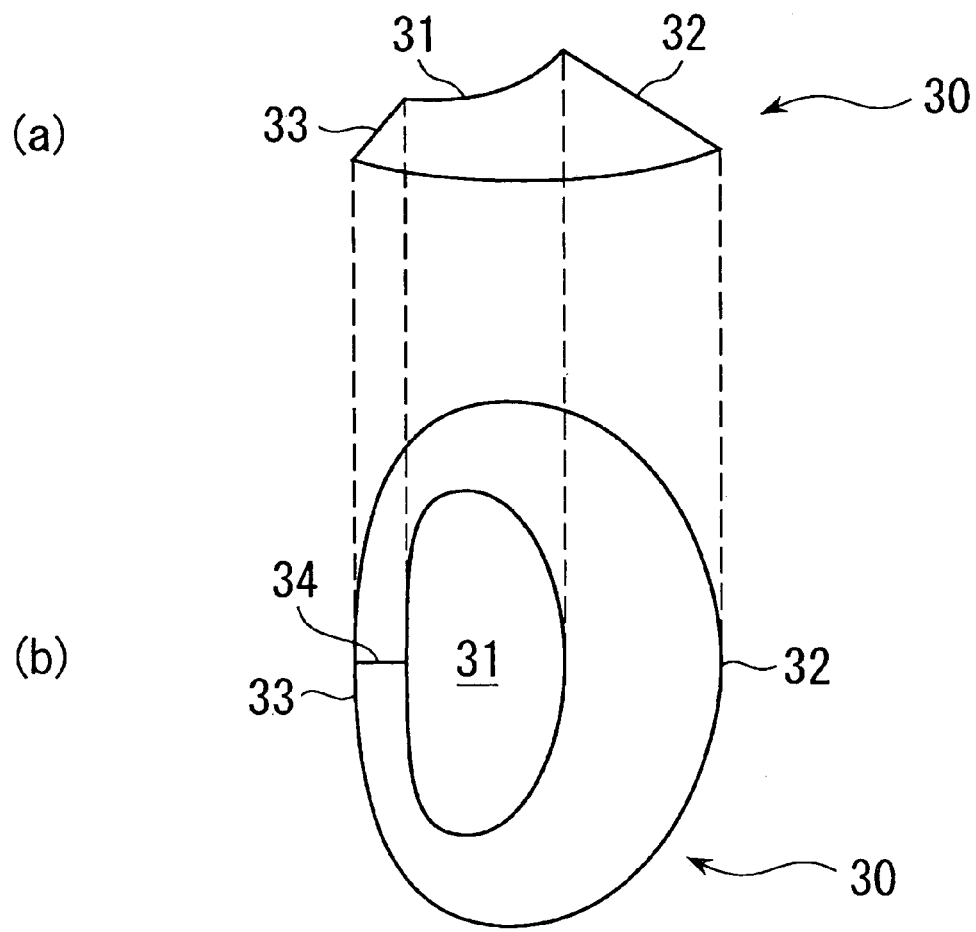
FIG. 4 is a schematic view, showing respectively top and side views of the insert.

An insert 30, formed of a plastic resin or other suitable flexible material, is generally in the form of a distorted, truncated cone, as shown in the upper part of FIG. 4. The insert has openings at both its wide and narrow ends, and a through passage extending from one of the openings to the other. The insert 30 is made by punching a C-shaped portion out of a sheet of material and joining the ends of the punched out portion together at a joint 34. As shown in the lower part of FIG. 4, the insert 30 comprises an oval opening 31 for receiving an external ear, and has a wide section 32 on one side of the opening and a narrow section 33 on the other side of the opening. The ends of the C-shaped portion can be joined by any of various methods. However, in the interest of strength and smoothness, a preferred method of joining the ends is ultrasonic welding, in which the ends of the C-shaped portion are welded by frictional heat, generated by ultrasonic energy while pressure is applied to the material. The distorted conical shape of the insert is determined by the angles at which the ends of the C-shaped portion are cut.

Figure 2:
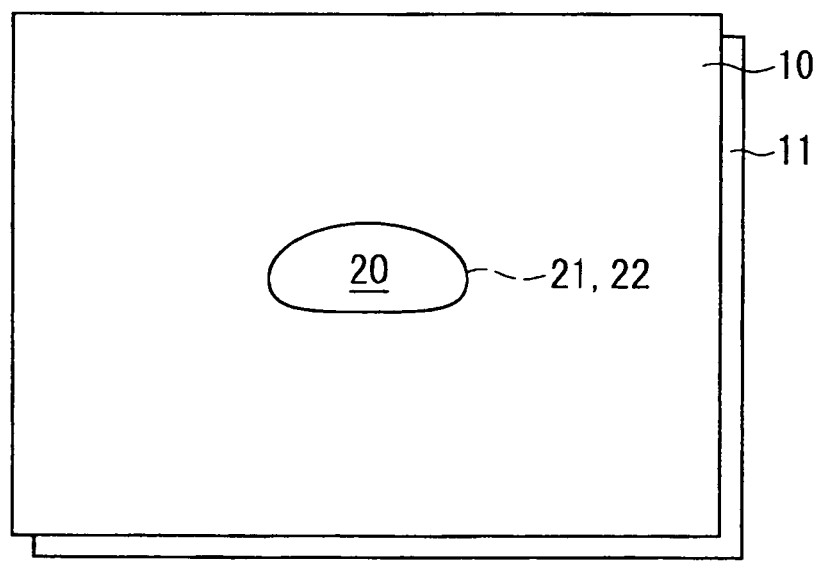
FIG. 2 is a top plan view, showing the stitched cloth layers turned inside-out so that the stitching is hidden between the cloth layers.
Figure 3:
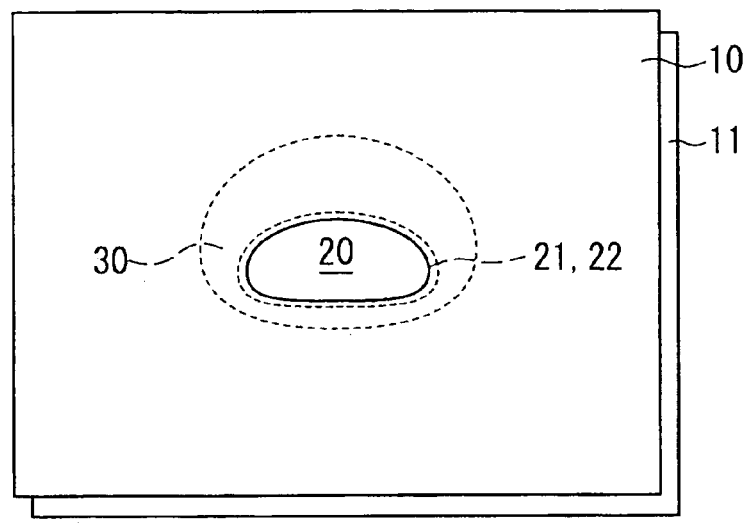
FIG. 3 is a top plan view, showing an insert in place between the cloth layers and surrounding the insertion hole.

One of the stitched cloth layers of the assembly of FIG. 2 is passed through the opening 31 of the insert, so that the insert is located between the cloth layers 10 and 11, and surrounds the outwardly turned stitched portion of the cloth assembly, as shown in FIG. 3. In FIG. 3, the smaller opening of the insert is in contact with cloth layer 10, while the larger opening is in contact with cloth layer 11. The shape of the insert 30 placed between the cloth layers is shown by broken lines.

Since the insert 30 is flexible, it can be shifted from one of two stable shapes to the other by the application of an external force. Thus, if a force is applied to the part of the insert having the smaller opening 31, the insert can be turned inside-out, so that the surface which forms the inside face of the distorted cone becomes an outside face. The shifting of the insert from one stable state to the other can be utilized by the wearer, as will appear below.

Figure 5:
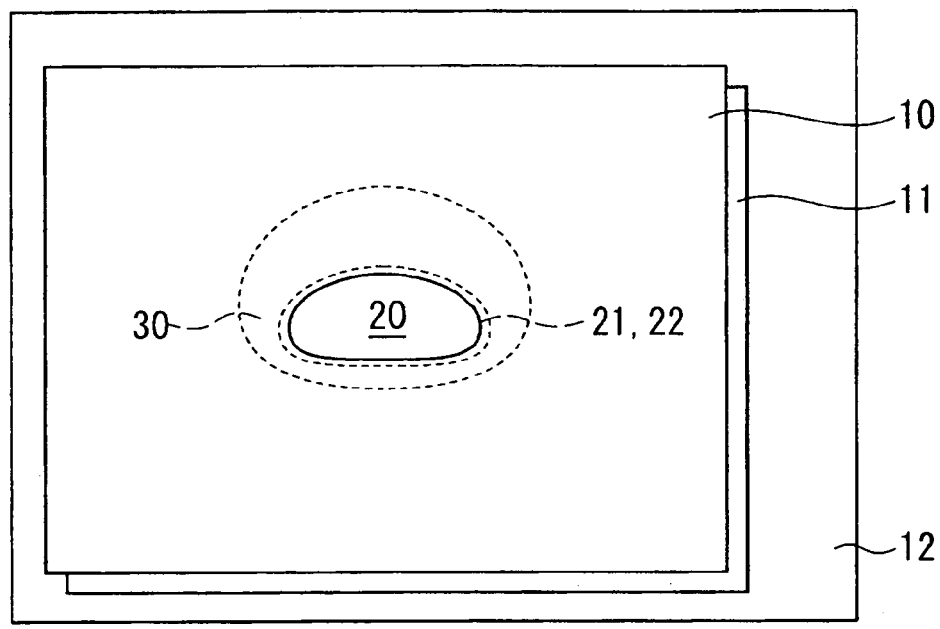
FIG. 5 is a top plan view, showing an additional cloth layer positioned underneath the assembly of FIG. 3.

After placing insert 30 between the cloth layer 10 and the cloth layer 11, a third cloth layer 12 is provided underneath cloth layer 11, as shown in FIG. 5. Thus, the third cloth layer 12 is on the outside face of cloth layer 11, the inside face of which is situated against the rim of the larger opening of the insert. The cloth layer 12 will become an outer covering of the final ear covering, and does not have an ear-receiving hole. Layer 12 will ordinarily be composed of more than one layer of cloth.

Figure 6:
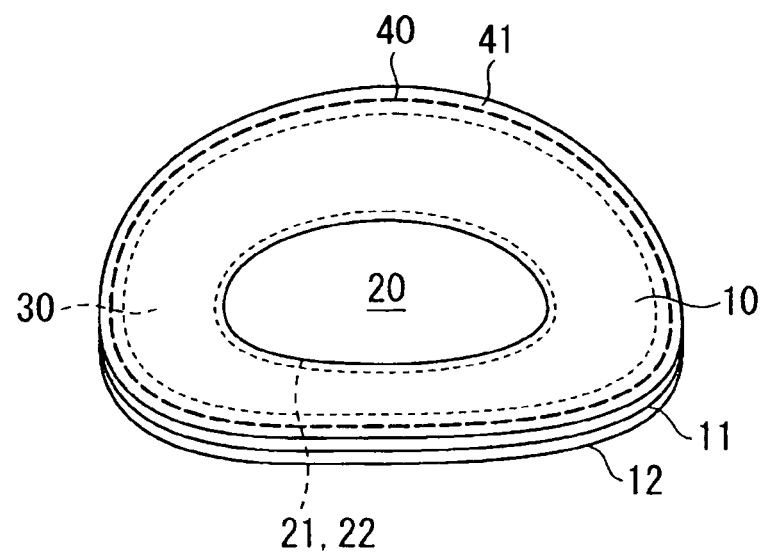
FIG. 6 is a perspective view showing all three cloth layers stitched together, with the insert between the uppermost two layers, and excess cloth removed.

The cloth layers 10, 11 and 12 are stitched together along seam 40 about the periphery of the insert 30 as shown in FIG. 6, and excess cloth is cut away leaving a small margin 41 surrounding the seam 40. Insert 30 is now completely enclosed in a toroidal enclosure formed by cloth layers 10 and 11, the peripheries of which are stitched together, and is completely invisible from the outside. The term "toroidal" is used herein as a short-hand way to describe a structure forming a passage in the form of a closed loop, and does not imply any specific passage cross-section or loop shape. As seen in FIG. 6, following the formation of seam 40, the ear covering is in a condition in which seam 40 and margin 41 are exposed and visible from the outside. The seam 40 and margin 41 are then hidden inside the ear covering by a turning operation in which the ear covering is turned inside out.

Figure 7:
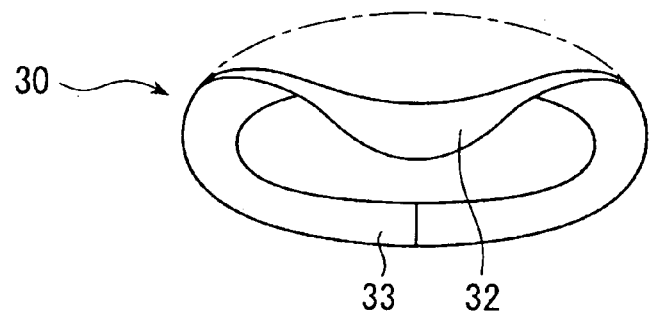
FIG. 7 is a schematic view illustrating an initial stage in the process of turning the ear covering inside-out, the view showing the insert with the cloth layers removed, for clarity.
Figure 8:
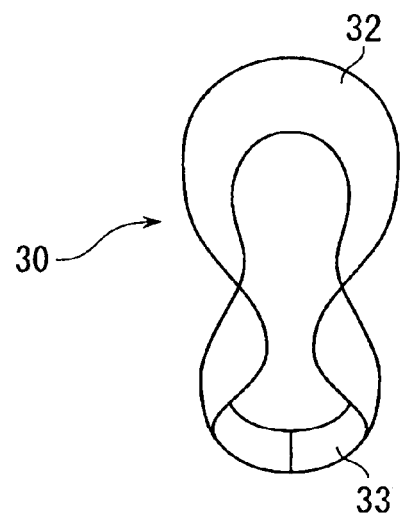
FIG. 8 is schematic view, similar to FIG. 7, illustrating a later stage in the process of turning the ear covering inside-out.

The method for turning an ear covering inside out is disclosed in U.S. Pat. No. 6,055,272, the disclosure of which is incorporated by reference. In order to show the process of turning the ear covering inside out more clearly, FIGS. 7 and 8 show only the insert 30. Briefly, as shown FIGS. 7 and 8, the widest part of the wide section 32 is pressed through opening 31, and the turning motion is continued along both sides of the ear covering until the narrow section 33 is pushed through the opening 31.

Figure 9:
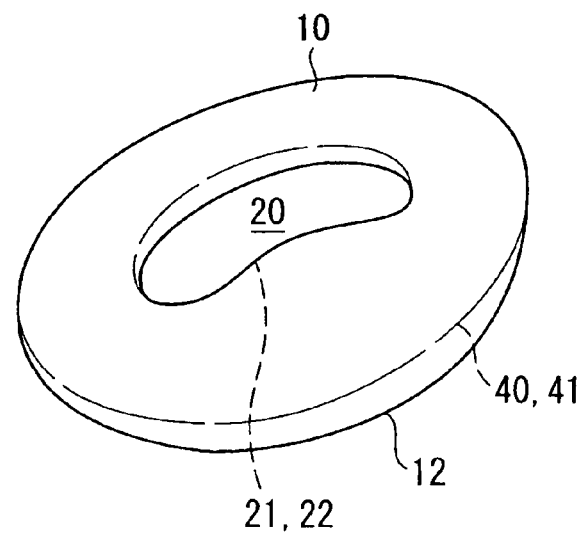
FIG. 9 is a perspective view showing the completed ear covering according to the invention.

FIG. 9 shows an example of the finished product. The stitching and the stitching margins of the cloth layers are hidden inside of the ear covering; and the insert is completely contained between two layers of cloth. Therefore, the ear covering of the invention prevents the wearer's ear from coming into direct contact with a bare insert making the ear covering more comfortable to use. In addition, the three-layered structure of the ear covering provides superior heat insulation and protection. Furthermore, the ear covering can be produced without complicated steps such as stitching the cloth to the insert, hemming the periphery of the insert, or adhering the cloth to the insert using an adhesive agent.

In using the ear covering of FIG. 9, the wearer, after inserting the external ear through the opening into the interior of the ear covering, can apply pressure to the insert, shifting the insert to its other stable state, so that the covering is firmly, but comfortably held on the external ear.

What is claimed is:

1. An ear covering comprising a first cloth layer, a second cloth layer, a third cloth layer and an insert with an opening for receiving an external ear;

said first and second cloth layers being stitched together along a first seam configured in a closed loop and having first margins extending beyond said first seam;

said first, second and third cloth layers being stitched together along a second seam also configured in a closed loop, said second seam being spaced from said first seam, and said first, second and third cloth layers having second margins extending beyond said second seam;

portions of said first and second cloth layers between said first and second seams forming a toroidal enclosure, and said insert being situated and enclosed within said enclosure;

said third layer extending across said toroidal enclosure and, with said first and second cloth layers, forming a cup-shaped receptacle for receiving an external ear;

said first margins being located within said toroidal enclosure; and said second margins being located inside said cup-shaped receptacle.

2. An ear covering as claimed in claim 1, wherein said insert is composed of a flexible material capable of being shifted, by the application of an external force, from one to the other of two different stable configurations, in each of which the insert is in the shape of a distorted, truncated cone.

3. A method for manufacturing an ear covering comprising a first cloth layer, a second cloth layer, a third cloth layer and an insert with a passage extending therethrough, said passage having opposite ends, and being open at both of said ends, one of said openings being adapted to receive an external ear, comprising the steps of:

placing the first and second cloth layers in facing relationship to each other;

stitching the first and the second cloth layers together along a first seam in the form of a closed loop;

forming an opening through said first and second layers within said closed loop;

turning said first and second cloth layers inside out by passing one of said cloth layers through said opening through the first and second layers;

following said turning step, passing one of the first and second cloth layers through the passage of the insert so that the insert surrounds said first seam;

positioning said third cloth layer adjacent one of said first and second cloth layers and across said opening through the first and second layers;

stitching the first, second and third cloth layers together along a second seam in the form of a closed loop surrounding the insert, thereby enclosing said insert within a toroidal enclosure formed by portions of said first and second cloth layers and forming an assembly consisting of said first, second and third cloth layers and said insert; and turning said assembly inside out by passing said third cloth layer at least part way through said insert, thereby forming a cup-shaped receptacle for receiving an external ear;

whereby margins of said first and second layers extending beyond said first seam are located within said toroidal enclosure and margins of said first, second and third layers extending beyond said second seam are located within the interior of said cup-shaped receptacle.

4. A method for manufacturing an ear covering as claimed in claim 3, wherein the step of forming an opening through said first and second cloth layers within said closed loop is carried out by forming holes in said first and second layers prior to the step of stitching said first and second cloth layers together.

* * * * *